(12) United States Patent
Jan et al.

(10) Patent No.: US 7,439,409 B1
(45) Date of Patent: Oct. 21, 2008

(54) PROCESS FOR PARA-XYLENE PRODUCTION FROM LIGHT ALIPHATICS

(75) Inventors: Deng-Yang Jan, Elk Grove Village, IL (US); Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 845 days.

(21) Appl. No.: 11/027,526

(22) Filed: Dec. 30, 2004

(51) Int. Cl.
*C07C 2/42* (2006.01)
*C07C 5/537* (2006.01)
*C07C 5/13* (2006.01)
*C07C 5/03* (2006.01)

(52) U.S. Cl. ............... 585/322; 585/418; 585/419; 585/654; 585/734; 585/251

(58) Field of Classification Search ............ 585/322, 585/418, 419, 654, 734, 251
See application file for complete search history.

(56) References Cited

U.S. PATENT DOCUMENTS

| 3,202,725 A | 8/1965 | Lorz et al. ............... 260/673.5 |
| 3,462,505 A | 8/1969 | Mooi et al. ............... 260/673.5 |
| 3,766,291 A | 10/1973 | Drehman ................ 260/673.5 |
| 4,169,865 A * | 10/1979 | Bamforth et al. ............ 585/314 |
| 4,367,356 A | 1/1983 | Ward ..................... 585/315 |
| 4,910,357 A | 3/1990 | Dessau et al. .............. 585/322 |
| 5,847,252 A | 12/1998 | Stine et al. ................ 585/330 |
| 5,856,604 A | 1/1999 | Stine et al. ................ 585/310 |
| 6,025,533 A | 2/2000 | Vora et al. ................ 585/330 |
| 6,177,601 B1 | 1/2001 | Bogdan et al. ............. 585/419 |
| 2004/0015026 A1 | 1/2004 | Manzer et al. ............. 585/418 |
| 2004/0044261 A1 | 3/2004 | Feng et al. ............... 585/419 |

FOREIGN PATENT DOCUMENTS

GB  795235  8/1958

OTHER PUBLICATIONS

Pines et al., Journal of Catalysis 1 (1962) pp. 313-328.
Canings et al., 1962 Radioisotopes Physical Science Industrial Process Conference, pp. 205-216.

* cited by examiner

*Primary Examiner*—Thuan Dinh Dang
(74) *Attorney, Agent, or Firm*—James C Paschall

(57) ABSTRACT

Low-value mixed butanes are processed to obtain a high yield of high-purity para-xylene. Processing steps may comprise fractionation to recover isobutane, dehydrogenation of the isobutane to isobutene, dimerization of the isobutene to obtain $C_8$ iso-olefins and isoparaffins, aromatization of the dimerized $C_8$ product, and recovery of high-purity para-xylene from the dimerized product by low-intensity crystallization. The availability of isobutane may be increased by isomerization of normal butane. Each of the processing steps may be tailored to the overall objective of high para-xylene yield from a relatively inexpensive feedstock.

17 Claims, 2 Drawing Sheets

PROCESS FOR PARA-XYLENE PRODUCTION FROM LIGHT ALIPHATICS

FIELD OF THE INVENTION

The present invention relates to the field of aromatic petrochemicals. More specifically, the invention relates to the production of para-xylene from light aliphatic hydrocarbons.

BACKGROUND OF THE INVENTION

Para-xylene is an important intermediate in the chemical and fiber industries. Terephthalic acid derived from para-xylene is used to produce polyester fabrics and other articles which are in wide use today.

Usually para-xylene is produced, in a series of steps, from naphtha fractionated from crude oil. Naphtha is hydrotreated and reformed to yield aromatics, which then are fractionated to separate typically benzene, toluene and $C_8$ aromatics comprising xylenes from $C_9$ and heavier aromatics. Toluene and $C_9$ aromatics may be disproportionated to yield additional xylenes. Xylene isomers, with the usual priority being para-xylene, are separated from the mixed $C_8$-aromatics stream using one or a combination of adsorptive separation, crystallization and fractional distillation, with adsorptive separation being most widely used in newer installations for para-xylene production. Other $C_8$ isomers may be isomerized and returned to the separation unit to yield additional para-xylene.

Although low-value light aliphatics such as butanes and butenes offer a substantial theoretical margin for the production of para-xylene, practical processes to effect this conversion have not been available to date. Butane dehydrogenation and dimerization plus aromatization to yield primarily octane isomers is taught in U.S. Pat. Nos. 5,847,252, 5,856,604 and 6,025,533. U.S. Pat. No. 4,367,356 discloses a combination of butene dimerization and alkylation to obtain $C_8$ hydrocarbons. These patents, whose relevant teachings are incorporated herein by reference, do not disclose the production of para-xylene.

In the Journal of Catalysis 1 (1962), pp. 313-328, Pines and Csicsery disclose the aromatization of trimethylpentanes to xylenes, using a nonacidic chromia-alumina catalyst; 2,2,4-trimethylpentane formed only para-xylene. In the proceedings of the 1962 *Radioisotopes Physical Science Industrial Process Conference* at pages 205-216, Cannings et al. teach dehydrocyclization of 2,2,4-trimethylpentane over a potassium- and cerium-promoted chromia-alumina catalyst to selectively yield para-xylene. British Patent 795,235 teaches the manufacture of para-xylene from 2,4,4-trimethylpentene using a catalyst comprising a Group VI-A oxide, exemplified as a series of chromia-containing catalysts. U.S. Pat. No. 3,202,725 discloses dehydrogenation of isobutane and recycle di-isobutylene using a chromia-alumina catalyst to yield para-xylene and isobutene, plus dimerization of the isobutene using a silica-alumina, phosphoric acid or sulfuric acid catalyst to yield primarily di-isobutylene recycle. U.S. Pat. No. 3,462,505 discloses the dehydrocyclization of 2,2,4-trimethylpentane to yield para-xylene using a catalyst comprising chromia, magnesia and an alkali metal on activated alumina. U.S. Pat. No. 3,766,291 discloses disproportionation of amylene to 2,5-dimethylhexene, which then is selectively converted to para-xylene over a catalyst comprising a Group II metal (exemplified by Zn) aluminate, tin-group metal, and Group VIII metal. U.S. Pat. No. 4,910,357 teaches the aromatization of dimethylhexanes, especially those contained in alkylate, using a catalyst comprising a dehydrogenation metal and a nonacidic crystalline support containing Sn, Tl, In and/or Pb. U.S. Pat. No. 6,177,601 B1 teaches aromatization of 2,5-dimethylhexane to selectively produce para-xylene, using a nonacidic L-zeolite catalyst. U.S. Publication 2004/0044261A1 teaches production of para-xylene from a feedstock rich in $C_8$ isoalkanes or isoalkenes using a catalyst comprising a molecular sieve, Group VIII metal and two or more of Si, Al, P, Ge, Ga and Ti. U.S. Publication 2004/0015026 discloses the manufacture of para-xylene from 2,2,4-trimethylpentane using a catalyst comprising chromium. It should be noted that chromium, as a catalyst constituent, is a toxic element.

None of the above references, drawn to the processing of particular feedstocks, discloses the selective process combination of the present invention. The art heretofore has not taught a practical process for the production of para-xylene from light hydrocarbons.

BRIEF DESCRIPTION OF THE INVENTION

In a broad embodiment this invention is a process combination for the production of para-xylene from isobutane. The process combination converts a feed stream comprising isobutane in a dehydrogenation zone with a dehydrogenation catalyst at dehydrogenation conditions to obtain an isobutene-containing intermediate stream. After separation of hydrogen, the isobutene-containing intermediate stream containing at least 50 wt.-% isobutane passes from the dehydrogenation zone and enters a dimerization zone. The dimerization zone contacts the intermediate stream with a solid dimerization catalyst at dimerization conditions to produce a butene dimer comprising iso-octenes. The dimerization zone effluent passes to an aromatization zone that converts olefins and paraffins by contact with an aromatization catalyst at aromatization conditions. Effluent from the aromatization zone is fractionated to recover mixed $C_8$ aromatics which pass to the separation zone for separation of para-xylene from residual $C_8$ aromatics. Preferably the separation comprises a single-stage crystallizer.

In a more specific embodiment, the process combination of the invention includes a deisobutanizer and, optionally, a butane-isomerization zone to provide an isobutane-containing feed stream to the process combination including processing of recycled $C_4$ materials. A mixed-butane feed, an isomerized stream from the butane-isomerization zone, and butanes recycled from the dehydrogenation-dimerization-aromatization combination provide feed to the deisobutanizer. A bottoms stream from the deisobutanizer passes to a butane-isomerization zone which converts a substantial portion of the normal butane in the bottoms-stream to isobutane, yielding an isomerized stream which is returned to the deisobutanizer. Isobutane from the deisobutanizer is processed in a dehydrogenation zone with a dehydrogenation catalyst at dehydrogenation conditions to obtain an isobutene-containing intermediate stream. After separation of hydrogen, the isobutene-containing intermediate stream containing at least 50 wt.-% isobutane passes from the dehydrogenation zone and enters a dimerization zone. The dimerization zone contacts the intermediate stream with a solid dimerization catalyst at dimerization conditions to produce a butene dimer comprising iso-octenes. The dimerization zone effluent passes to an aromatization zone that converts olefins and paraffins by contact with an aromatization catalyst at aromatization conditions. Effluent from the aromatization zone is fractionated to recover mixed $C_8$ aromatics which pass to the separation zone for separation of para-xylene from residual $C_8$ aromatics. Preferably the separation comprises a single-stage crystallizer.

DETAILED DESCRIPTION OF THE INVENTION

The process combination and individual operational steps will be described in conjunction with FIGS. 1 and 2. The figures show only those portions of the process that are necessary to gain an understanding of the invention and the means of integrating the different process steps that comprise the invention. Further details related to heaters, coolers, exchangers, valves, control means, pumps, compressors, and other necessary processing equipment are well known to those skilled in the art and not described in detail unless necessary for an understanding of the invention. Also, these descriptions do not exclude from the inventive concept other embodiments which may result from the modification of the descriptions by a skilled routineer.

Figure 1:
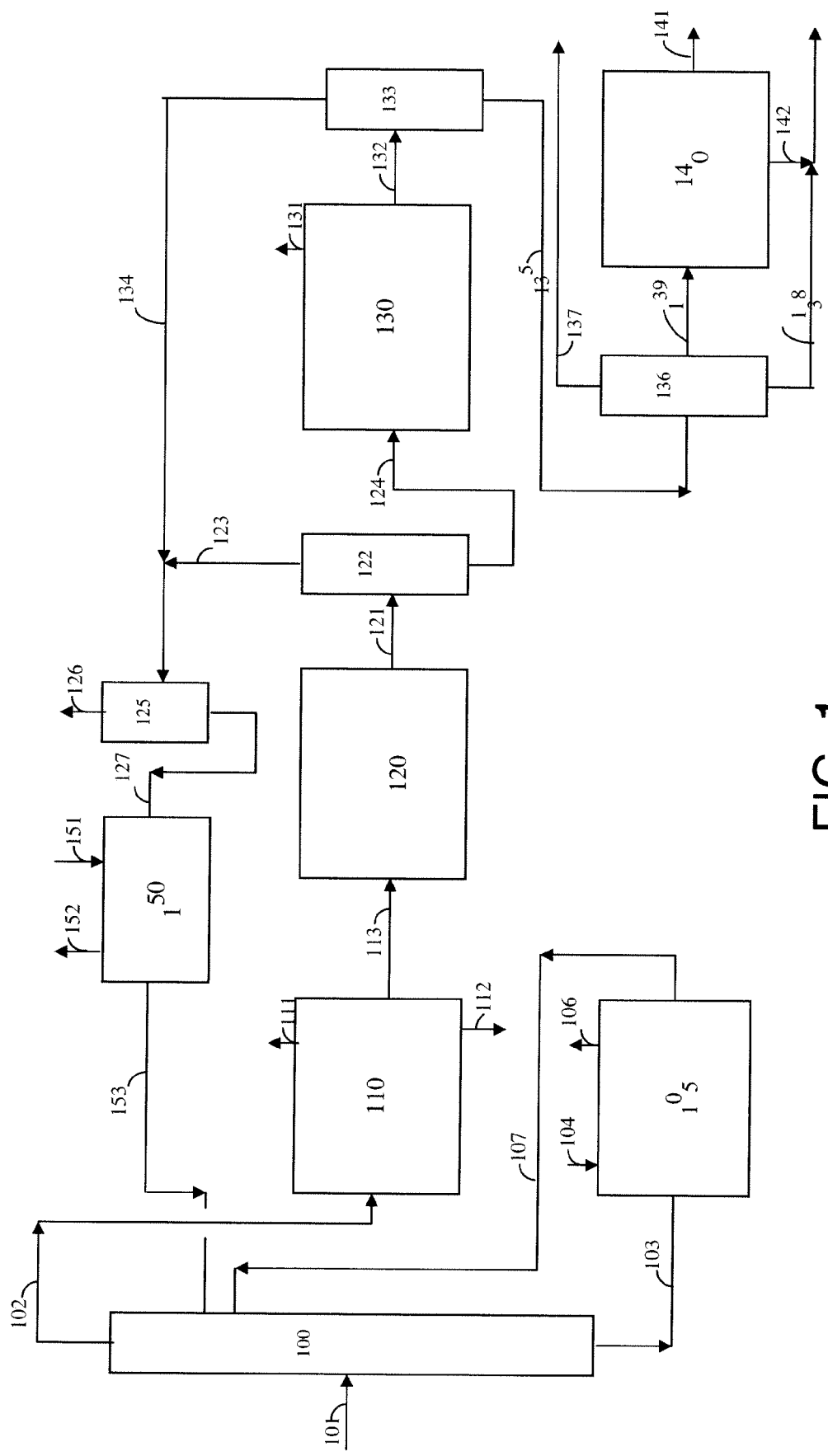
FIG. 1 is a schematic process flow diagram of the invention when processing mixed butanes to yield para-xylene.

FIG. 1 is a block flow diagram illustrating the process combination of the invention when processing a mixed-butane feed stream. Deisobutanizer 100 processes primary feed stream 101, which comprises a mixture of isobutane and normal butane, along with recycle streams 153 and 107 discussed hereinafter. The deisobutanizer separates the entering process streams into a net overhead stream in line 102 which is rich in isobutane and bottoms stream in line 103 which is rich in normal butane. If the feed streams contain a substantial amount of propane, the isobutane-rich stream may be recovered as a sidestream from the upper part of the deisobutanizer with the propane taken overhead; however, this introduces inefficiencies through the higher column pressures required. Similarly, if the feed streams contain a substantial amount of pentanes, the normal-butane concentrate may be taken as a lower sidestream from the deisobutanizer with the heavier material as a bottoms fraction.

If production of additional isobutane for the process is advantageous, the normal-butane concentrate in line 103 is charged, along with hydrogen in line 104, to a butane-isomerization zone 105. In this zone, the feeds are contacted with a butane isomerization catalyst maintained at conditions effective to convert at least a substantial portion of the entering normal butane into isobutane. The light ends which are produced during the isomerization of the normal butane are removed from this zone in line 106. The resulting isomerized product stream of the butane isomerization zone is returned in line 107 to the deisobutanizer column 100 at an intermediate point, usually above the feed line 101, because this stream is relatively rich in isobutane.

The isobutane-rich stream taken overhead from the deisobutanizer is charged via line 102 to the dehydrogenation zone 110. A small amount of sulfur may be added to this stream to prevent carbon formation on metallic surfaces of the dehydrogenation reactors and heaters and to passivate the catalyst. This zone at least partially dehydrogenates isobutane and other lesser feed components to yield hydrogen, isobutene, some light hydrocarbons and small amounts of heavy hydrocarbons comprising mainly xylenes and aromatics. Usually hydrogen is recycled within the unit, with a net hydrogen stream produced via line 111. The hydrogen usually has a purity between about 70 and about 90 mol-%.

Dehydrogenation zone 110 usually comprises two or more reactors and a catalyst regeneration system, as described in detail hereinafter. The regeneration system comprises a transfer system from and to the reactors and a facility to recondition catalyst by coke combustion and re-dispersion of active components.

Preferably a separator within zone 110 removes a heavy hydrocarbon component, comprising principally xylenes and other aromatics, from the dehydrogenation-zone effluent stream via line 112; this stream may advantageously be processed for para-xylene recovery along with the effluent of the aromatization zone 130 as discussed hereinafter. An optional further separation may be made, e.g., via a stripper/fractionator, of $C_3$ and lighter components in order to concentrate the isobutene for further processing. The principal product 113 of the dehydrogenation zone, comprising largely isobutene and unconverted isobutane, is directed via line 113 to dimerization zone 120.

In the dimerization zone 120, the dehydrogenation zone product passes through a series of dimerization reactors. Zone 120 is divided into multiple reactor stages in order that the dimerization reaction temperature can be controlled by injection of quench between stages. The isobutene is selectively dimerized to form primarily branched $C_8$ olefins. Effluent from the dimerization reactors is stabilized in unit 122 to separate $C_4$ and lighter products, with the butene dimer passing to the aromatization zone 130 via line 124.

The aromatization zone converts the butene dimer from zone 120 to yield a high proportion of para-xylene. The aromatization zone typically uses a plurality of reactors arranged in series with the entire feed passing through each reactor. Since the aromatization reaction is highly endothermic, a series of reactors with reheating between each reactor permits greater control of the processing temperature. Hydrogen generated by aromatization is circulated within the aromatization zone, with a net hydrogen stream produced via line 131. Liquid effluent from aromatization passes via line 132 to unit 133 to separate $C_4$ and lighter products via stabilization in line 134. Debutanized product from 133 passes in line 135 to unit 136 for further separation of products. Unit 136 may be a sidestream fractionator as shown, or it may comprise two or more fractionating columns. In any event, a stream comprising $C_5$ to $C_7$ hydrocarbons is removed in line 137 and a stream comprising $C_9$ and heavier hydrocarbons is removed in line 138 in order to provide a para-xylene concentrate 139 as feed to para-xylene-recovery zone 140.

$C_4$ and lighter streams in line 134 from fractionation of aromatization product and line 123 from fractionation of the butene dimer may be returned to other refining and petrochemical facilities for recovery of butane and butane values. Optionally, these streams may be processed within the present process combination as shown to recycle butanes to the deisobutanizer. Streams 134 and 123 are processed in a stripper/fractionator 125 to remove $C_3$ and lighter materials. Stripper bottoms in line 127 are hydrogenated in saturation zone 150, with hydrogen supplied in line 151, to convert butenes to butanes. After removal of light materials in line 152, the butanes are sent in line 153 to deisobutanizer 100 to recover additional isobutane and normal butane for processing according to the process combination.

Separation zone 140 may comprise any suitable process to recover para-xylene of the desired purity, usually >99.7% purity, including without limitation one or more of continuous adsorption, pressure-swing adsorption, fractionation and crystallization. Single-stage crystallization is preferred as a relatively inexpensive technique to separate high-purity para-xylene in line 141 from a feed rich in the para-isomer. The reject stream in line 142 is rich in other $C_8$-aromatics isomers. Streams 137, 138 and 142 all are suitable components for gasoline blending, being rich in high-octane aromatics.

The primary feed typically comprises a refinery paraffin stream that preferably contains at least 20 wt.-% isobutane. Preferred feeds for the present process are rich in isobutane and will more preferably have an isobutane concentration in a range of from 55 to 99 wt.-%. Typical sources for this feedstream are field butanes, refinery C4 saturate streams, effluents from butane isomerization, and butanes from gas recovery units. Feeds having lower isobutane contents can be processed according to the process, but usually would be isomerized to increase the isobutane content before passing to the deisobutanizer. In the event that high-purity isobutane, i.e., having a purity of at least about 80 wt.-% and preferably about 95 wt.-% or more, is available within an existing complex, the deisobutanizer can be omitted according to the scheme in FIG. 2.

Figure 2:
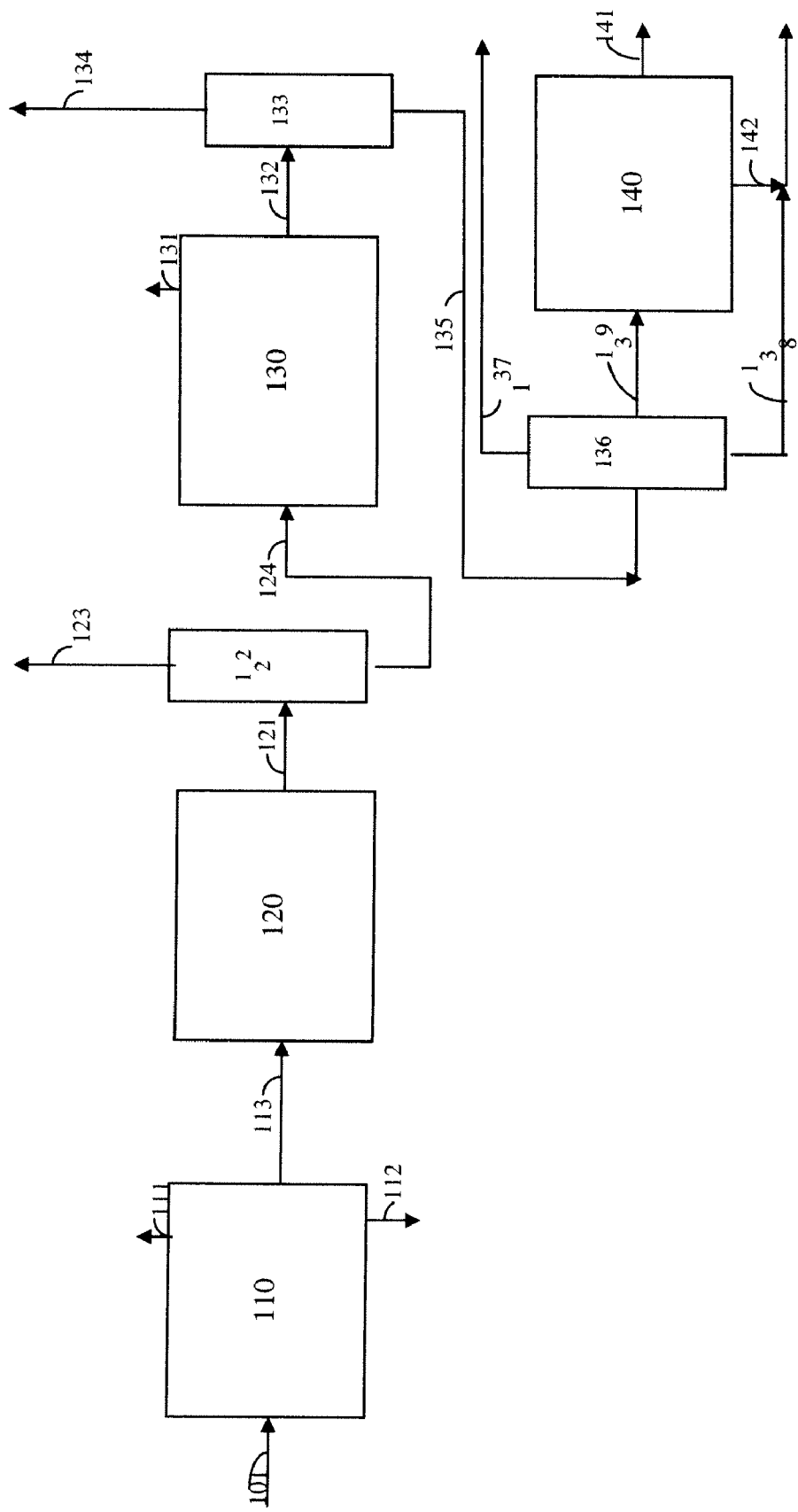
FIG. 2 is a schematic process flow diagram of the invention when processing an isobutane concentrate to yield para-xylene.

FIG. 2 is a block flow scheme illustrating an embodiment of the process combination of the invention when processing an isobutane-rich feed. Line 101 passes the isobutane feed into dehydrogenation zone 110, which converts at least a portion of the isobutane to yield primarily isobutene. Zone 110 usually comprises two or more reactors and a catalyst regeneration system as described in detail hereinafter. The regeneration system comprises a transfer system from and to the reactors and a facility to recondition catalyst by coke combustion and re-dispersion of active components.

Preferably a separator within zone 110 removes a heavy hydrocarbon components, comprising principally xylenes and other aromatics, from the dehydrogenation-zone effluent stream via line 112; this stream may advantageously be processed for para-xylene recovery along with the effluent of the aromatization zone 130 as discussed hereinafter. An optional further separation may be made, e.g., via a stripper/fractionator, of $C_3$ and lighter components in order to concentrate the isobutene for further processing. The principal product 113 of the dehydrogenation zone, comprising largely isobutene and unconverted isobutane, is directed via line 113 to dimerization zone 120.

In the dimerization zone 120, the dehydrogenation zone product passes through a series of dimerization reactors. Zone 120 is divided into multiple reactor stages in order that the dimerization reaction temperature can be controlled by injection of quench between stages. The isobutene is selectively dimerized to form primarily branched $C_8$ olefins. Effluent from the dimerization reactors is stabilized in unit 122 to separate $C_4$ and lighter products, with the butene dimer passing to the aromatization zone 130 via line 124.

The aromatization zone converts the butene dimer from zone 120 to yield a high proportion of para-xylene. The aromatization zone typically uses a plurality of reactors arranged in series with the entire feed passing through each reactor. Since the aromatization reaction is highly endothermic, a series of reactors with reheating between each reactor permits greater control of the processing temperature. Hydrogen generated by aromatization is circulated within the aromatization zone, with a net hydrogen stream produced via line 131. Liquid effluent from aromatization passes via line 132 to unit 133 to separate $C_4$ and lighter products via stabilization in line 134. Debutanized product from 133 passes in line 135 to unit 136 for further separation of products. Unit 136 may be a sidestream fractionator as shown, or it may comprise two or more fractionating columns. In any event, a stream comprising $C_5$ to $C_7$ hydrocarbons is removed in line 137 and a stream comprising $C_9$ and heavier hydrocarbons is removed in line 138 in order to provide a para-xylene concentrate 139 as feed to para-xylene-recovery zone 140.

Zone 140 may comprise any suitable process to recover pure para-xylene (usually >99.7% purity) from the concentrate in line 139, including without limitation one or more of continuous adsorption, pressure-swing adsorption, fractionation and crystallization. Single-stage crystallization is preferred as a relatively inexpensive technique to separate high-purity para-xylene in line 141 from a feed rich in the para-isomer. The reject stream in line 142 is rich in other $C_8$-aromatics isomers. Streams 137, 138 and 142 all are suitable components for gasoline blending, being rich in high-octane aromatics.

A deisobutanizer as indicated in FIG. 1 primarily separates isobutane as a top stream from normal butane as a bottoms stream. Integration of multiple feed inputs and stream outputs on the deisobutanizer column promote separation efficiency by permitting matching of stream compositions with column locations in a manner that reduces the overall size of the deisobutanizer column. The deisobutanizer will typically provide an isobutane purity of 80 wt.-% and more preferably at least 95 wt.-%. Usually isobutane is taken overhead from the deisobutanizer, but may be recovered as a sidestream from the top section of the deisobutanizer if propane and lighter components are present in the feed in a significant concentration with propane taken overhead from the column. If C5 and heavier material is present in the feed in any significant concentration, a normal-butane concentrate may be recovered as a lower sidestream from the deisobutanizer with the C5 and heavier material as a bottoms product. Preferably the C5 and heavier material, and especially the C3 and lighter material, are removed from the mixed butane stream in prior fractionation.

Optionally, the normal-butane concentrate is sent to an isomerization zone to obtain additional isobutane for input to the process. This zone comprises a reactor and a stripping column. Isomerization conditions comprise a relatively low pressure, usually from about 0.5 to 3.5 MPa, and at an elevated temperature as required by the activity of the catalyst. The average reaction temperature may be as high as 500° C., but is preferably between 100° and 320° C. It is normal practice to pass the butane through the reactor in admixture with between 1 and 10 moles of hydrogen per mole of butanes to ensure vapor phase conditions and to suppress coke deposition on the catalyst. It is preferred that the butane contacts an isomerization catalyst in one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and a liquid isomerized product. The aforementioned stripping column eliminates residual hydrogen and light ends (C3 and lighter) and also, when using the preferred catalyst, volatile chloride compounds. The isomerized product is returned to the deisobutanizer for recovery of contained isobutane.

Any catalyst known in the art to be suitable for the isomerization of paraffin-rich hydrocarbon streams may be used as an isomerization catalyst in the isomerization zone. A preferred isomerization catalyst composition comprises one or more platinum-group metals, a halogen, and an inorganic-oxide binder. Preferably the catalyst contains a Friedel-Crafts metal halide, with aluminum chloride being especially preferred. The optimal platinum-group metal is platinum which is present in an amount of from about 0.1 to 0.5 wt.-%. The composition may also contain an organic polyhalo component, with carbon tetrachloride being preferred, and the total chloride content is from about 2 to 10 wt.-%. The inorganic oxide preferably comprises alumina, with one or more of gamma-alumina and eta-alumina providing best results. Optimally, the carrier material is in the form of a calcined cylindrical extrudate. An organic chloride promoter is required to maintain a high level of active chloride on the preferred catalyst. The concentration of promoter in the combined feed is maintained at from 30 to 300 wt. ppm. U.S. Pat. Nos. 2,999,074 and 3,031,419 teach additional aspects of this composition and are incorporated herein by reference.

Other suitable isomerization catalysts comprise a platinum-group metal, hydrogen-form crystalline aluminosilicate and a refractory inorganic oxide. The preferred noble metal is platinum which is present in an amount of from about 0.01 to 5 wt.-% of the composition, and optimally from about 0.15 to 0.5 wt.-%. Catalytically effective amounts of one or more promoter metals preferably selected from Groups VIB(6), VIII(8-10), IB(11), IIB(12), IVA(14), rhenium, iron, cobalt, nickel, gallium and indium also may be present. The crystalline aluminosilicate may be synthetic or naturally occurring, and preferably is selected from the group consisting of FAU, LTL, MAZ and MOR with mordenite having a silica-to-alumina ratio of from 16:1 to 60:1 being especially preferred. The crystalline aluminosilicate generally comprises from about 50 to 99.5 wt.-% of the composition, with the balance being the refractory inorganic oxide. Alumina, and preferably one or more of gamma-alumina and eta-alumina, is the preferred inorganic oxide. Further details of the composition are disclosed in U.S. Pat. No. 4,735,929, incorporated herein by reference thereto.

Water and sulfur are catalyst poisons especially for the chlorided platinum-alumina catalyst composition described hereinabove. Water can act to permanently deactivate the catalyst by removing high-activity chloride from the catalyst and replacing it with inactive aluminum hydroxide. Therefore, water and oxygenates that can decompose to form water can only be tolerated in very low concentrations. In general, this requires a limitation of oxygenates in the feed to about 0.1 ppm or less. Sulfur present in the feedstock serves to temporarily deactivate the catalyst by platinum poisoning. The present isomerization feed is not expected to contain a significant amount of sulfur.

The isobutane-rich top stream from the deisobutanizer passes to the dehydrogenation reaction zone. This zone utilizes any type of reactor configuration that efficiently dehydrogenates isobutane to isobutene. The particular dehydrogenation reactor configuration will depend, inter alia, on the performance characteristics of the catalyst. The olefin yield from the dehydrogenation reactor will usually be in a range of 10 to 60 wt.-% and more typically in a range of from 20 to 50 wt.-%. Low-conversion conditions within the dehydrogenation zone extend the life of the dehydrogenation catalyst. Low-conversion conditions will usually give the catalyst a cycle life usually of at least one month or more. Any suitable method can regenerate the catalyst such as a swing bed or continuous catalyst regeneration procedures.

Depending on the catalyst system and the properties of the dehydrogenation zone feed, the dehydrogenation reaction zone will use a solid dehydrogenation catalyst that can operate as a fixed bed, a semi-regenerated bed or continuous catalyst regeneration. The arrangement of the dehydrogenation zone may be relatively simple and include a single reactor and single heater. Alternatively, the dehydrogenation catalytic reaction zone may consist of multiple catalyst beds. In one such system, the catalyst is employed within an annular bed through which it is movable via gravity flow.

In preferred form, the dehydrogenation process will employ a moving-bed reaction zone and regeneration zone. Moving-bed systems advantageously maintain production while the catalyst is removed or replaced. In a typical moving bed reaction zone fresh catalyst particles are fed through the reaction zones by gravity. Catalyst is withdrawn from the bottom of the reaction zone and transported to a regeneration zone where a multi-step regeneration process is used to recondition the catalyst to restore its full reaction promoting ability. Catalyst flows by gravity through the various regeneration steps and then is withdrawn from the regeneration zone and furnished to the reaction zone. Movement of catalyst through the zones is often referred to as continuous though, in practice, it is semi-continuous. By semicontinuous movement is meant the repeated transfer of relatively small amounts of catalyst at closely spaced points in time.

Most typical multireactor arrangements for the dehydrogenation zone will have interstage heating between reactors that establish adiabatic conditions through the reactors. Further improvements in catalyst life and reactor stability may be obtained by operating the reactor isothermally or with an ascending temperature profile over the reactant path of the reactor. Isothermal conditions or ascending temperature profiles may be established by indirect heat exchange between the reactants or catalyst beds within the reaction zone and a circulating heat-exchange medium. Such reactor arrangements can include internal heating means within the catalyst bed. Useful arrangements for internal heating of reactants can employ tubes or channels for indirect heating with catalyst and reactants on one side of a heat exchange surface and a heating medium on the opposite side. Other heating arrangements for the reactor bed may integrate a fired heater wherein catalyst is contained within tubes that occupy the combustion chamber of the heater.

During the course of a dehydrogenation reaction, catalyst particles become deactivated as a result of mechanisms such as the deposition of coke on the particles; that is, after a period of time in use, the ability of catalyst particles to promote dehydrogenation reactions decreases to the point that the catalyst is no longer useful. The catalyst must be reconditioned or regenerated to restore its effectiveness in promoting dehydrogenation reactions. In such systems, it is common practice to remove catalyst from the bottom of the reaction zone, regenerate it and then return it to the top of the reaction zone. Preferred methods of dehydrogenating light hydrocarbons, suitable for the continuous dehydrogenation of isobutane, using a continuous catalyst regeneration system are described in U.S. Pat. Nos. 5,227,566; 5,847,252; 5,856,604; and 6,025,533, the contents of which are hereby incorporated by reference.

In the preferred regeneration method for the dehydrogenation process of this invention, catalyst is contacted with a hot oxygen-containing gas stream (known as recycle gas) in order to remove coke which accumulates on surfaces of the catalyst while it is in a dehydrogenation reaction zone. Coke comprises primarily carbon but also contains a relatively small quantity of hydrogen. The mechanism of coke removal is oxidation to carbon monoxide, carbon dioxide, and water. Coke content of spent catalyst may be as much as 20% of the catalyst weight, but 5-7% is a more typical amount. Within the combustion zone, coke is usually oxidized at temperatures ranging from about 470° C. to about 540° C., but temperatures in localized regions may reach 600° C. or more.

Oxygen for the combustion of coke usually enters a combustion section of the regeneration zone in a recycle gas. The recycle gas contains a low concentration of oxygen, usually on the order of 0.5 to 1.5% by volume, to maintain temperature control. The remainder of the recycle gas is usually composed of mainly of inert combustion by-products. A system of blowers, heaters and coolers maintain circulation and the temperature of the recycle gas in the regeneration zone.

It is also possible to use steam as a diluent for the combustion gas stream and avoid the circulation of recycle gas. The low-severity conversion conditions within the dehydrogenation zone result in a low coke load on the regeneration zone. The low coke loading requires only a small regeneration zone to provide sufficient coke combustion. Relatively small amounts of steam can be used to dilute an oxygen containing stream to sufficiently low $O_2$ levels for a controlled heat release in the regeneration zone.

In addition to combustion the regeneration normally includes steps of drying and redispersion. Exposure to reactants in a wet reduction zone and the exposure to high temperatures and steam in the combustion zone serves to agglomerate the platinum on the surface of the catalyst. Once the coke has been removed and residual water evaporated, and the catalyst particles are in various states of oxidation, contact of the catalyst at a temperature between about 425° C. and 600° C. in a chlorine environment will re-disperse the platinum over the surface of the catalyst support.

Operating conditions for the dehydrogenation reaction zone are specifically selected to provide low conversion. Conversion usually is within the range of about 10% to 60%, without so limiting the invention, and a preferable range is from about 20% to 50%. Preferred dehydrogenation conditions usually include an operating temperature in the range of from 510° to 650° C., with an operating temperature of at least 595° C. being preferred and with an operating temperature of about 610° C. being particularly preferred. A relatively high operating pressure characterizes the low-conversion conditions of the preferred dehydrogenation zone and is usually within a range of 100 to 800 kPa, with pressures of about 100 to 600 kPa being particularly preferred. Low-conversion conditions will also permit the operation of the dehydrogenation zone at low hydrogen to hydrocarbon ratios in a range of from 0.1 to 4 and more preferably about 0.2. Space velocities for the dehydrogenation zone range from 0.5 to 50 and will normally exceed 10 and typically equal about 15. Further extension of the catalyst life may be obtained by operating with lower space velocities.

Optionally, the dehydrogenation and dimerization reaction zones can be integrated through high-pressure and low-conversion dehydrogenation conditions. The higher pressure and lower conversion will reduce catalyst deactivation and allow most dehydrogenation reaction zones to operate with reduced regeneration requirements. In addition higher pressure conditions in particular reduce compression requirements for effluent separation and improve process efficiency. The lower-severity dehydrogenation zone reaction conditions also provide the unreacted mass flow of butane for temperature control necessary for the dimerization reaction.

Any suitable dehydrogenation catalyst may be used in the process of the present invention. A catalytic dehydrogenation reaction is normally effected in the presence of a catalyst comprising one or more Group VIII noble metals (e.g., platinum, palladium, iridium, rhodium) combined with a porous carrier, such as a refractory inorganic oxide. Generally, the preferred catalyst comprises a platinum group metal component, an alkali metal component and a porous carrier. The catalyst may also contain metal modifiers which advantageously improve the performance of the catalyst.

Preferably the porous carrier material is an absorptive high-surface-area support having a surface area of about 25 to about 500 m$^2$/g. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxides, magnesia, silica alumina, alumina boria; crystalline alumina silicates such as naturally occurring or synthetically prepared mordenite or a combination of one or more of these materials or other zeolite materials. The preferred porous carrier material is a refractory inorganic oxide, with the best results being obtained with an alumina carrier material. Alumina is the most commonly used carrier. The preferred alumina materials are known as the gamma, eta and theta alumina with gamma and theta alumina giving the best results. The preferred catalyst will have a theta alumina carrier which is in the form of spherical particles. Particles having relatively small diameters on the order of about 1.5 mm are preferred, but the particles may be as large as 6 mm.

Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all of the platinum group components exist in the elemental state. The platinum group components generally comprises from about 0.01 to about 2 wt.-% of the final catalytic composite, calculated on an elemental basis. It is preferred that the platinum content of the catalyst be between about 0.2 and 1 wt.-%. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

The preferred alkali metal is normally either potassium, cesium or lithium, depending on the feed hydrocarbon. The concentration of the alkali metal may range from about 0.1 to 3.5 wt.-%, but is preferably between 0.2 and about 2.5 wt.-% calculated on an elemental basis. This component may be added to the catalyst by the methods described above as a separate step or simultaneously with the solution of another component.

As noted previously, the dehydrogenation catalyst may also contain a metal modifier. One such preferred promoter metal is tin. The tin component should constitute about 0.01 to about 1% tin. It is preferred that the atomic ratio of tin to platinum be between 0.1:1 and about 6:1. The tin component may be incorporated into the catalytic composite in any suitable manner known to effectively disperse this component in a very uniform manner throughout the carrier material. A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of platinum component and the tin component to the carrier material may be obtained by reference to U.S. Pat. No. 3,745,112.

Higher pressures within the dehydrogenation zone can result in the production of a hydrogen stream having purities of 80% or greater with minimal cooling. The effluent from the dehydrogenation also may pass to a separator for removal of aromatics that are produced as the by-products from the dehydrogenation process and, optionally, stabilization to remove light byproducts. Apart from heat exchange and pressurization all remaining portions of the dehydrogenation zone, the dehydrogenation product passes directly to the dimerization zone.

Suitable dimerization zones for this invention may be known by a variety of names and employ one or more of several catalyst types. Other names for the dimerization zone include oligomerization, catalytic condensation and catalytic polymerization. The use of resin catalysts for effecting dimer production is described, for example, in U.S. Pat. Nos. 4,100,220; 4,215,011; and 4,302,356. The use of a layered molecular sieve for isobutene oligomerization is taught in U.S. Pat. No. 6,649,802 B1. U.S. Pat. No. 6,689,927 B1 discloses oligomerization of isobutene using a solid phosphoric acid catalyst. The applicable teachings of all of the above references in this paragraph are incorporated herein by reference thereto. An effective dimerization zone provides a high yield of iso-octenes and iso-octanes having a high concentration of one or more of 2,4,4-trimethylpentene, 2,2,4-trimethylpentane, 2,5-dimethylhexene and 2,5-dimethylhexane in the product from the zone.

The dimerization zone alternatively may comprise alkylation of isobutane with butenes to provide a suitable feedstock for the aromatization step; the integration of an alkylation unit with a dehydrogenation unit is described, for example, in U.S. Pat. No. 4,275,255, incorporated herein by reference thereto. An isobutane-containing stream and the dehydrogenation product stream or the dehydrogenation product stream that containing isobutylene and isobutane are contacted in the dimerization zone with an alkylation catalyst to produce a butene dimer which comprises a high concentration of $C_8$ isoparaffins. One typical product from the alkylation of isobutene with isobutane had the following yield structure in wt.-%:

|                        |       |
|------------------------|-------|
| Lighter than $C_8$     | 3.6   |
| 2,2,4-trimethylpentane | 67.3  |
| 2,3,4-trimethylpentane | 13.0  |
| 2,3,3-trimethylpentane | 7.2   |
| Dimethylhexanes        | 3.5   |
| Heavier than $C_8$     | 5.4   |

A dimerization catalyst preferably is disposed in fixed beds within the dimerization zone in what is known as a chamber-type reactor structure. In a chamber-type reactor, the reactants flow through one or more fixed catalyst beds. The temperature gradient within the reactor from the exothermic dimerization reaction is controlled by recycling relatively inert hydrocarbons which act as a heat sink. The unreacted isobutane from the dehydrogenation zone supplies a large proportion of the inert hydrocarbons that act as the heat sink. The temperature gradient within the dimerization reaction zone also may be controlled by the use of a quench material between the catalyst beds. As a secondary purpose, the quench material can provide a flushing function to inhibit the development of coke and the deactivation of coke in the deactivation of the catalyst within the reaction zones. Unconverted isobutene, containing unconverted butanes from the dehydrogenation zone, from stabilization of the butene dimer may be used as quench. Higher molecular weight quench material may be used within the dimerization reaction zones to flush the catalyst and preventing coke production. The recycle of such materials as the $C_5$ to $C_7$ byproduct from the aromatization zone can also improve selectivity of the dimerization zone to produce the desired $C_8$ products. Since the higher molecular weight materials have benefits beyond use as a quench, it can be beneficial to add all or a portion of such material to the inlet of dimerization reactor with the feed.

A particularly preferred dimerization catalyst is a cationic resin catalyst such as the Amberlyst series (for example, Amberlyst 15) as produced by Rohm & Haas. The present process preferably is carried out in a substantially vertical fixed catalyst bed; for example, a bed of cation exchange resin supported in a vertical reactor. The flow in the reactor may be upward or downward, with downflow being preferred. Generally, the liquid hydrocarbon and an optional water, ether and/or alcohol cofeed may pass through a single line or separate lines into the reactor. A preferred cofeed concentration is an equivalent of 0.001 to 1 mol of t-butanol per mol of isobutene.

A range of yields may be effected by varying conversion, as illustrated by the following yields from a feedstock containing 43.5 wt.-% isobutene and 1.5 wt.-% normal butene with the balance being primarily butanes:

| Isobutene conversion, %                 | 49.6 | 68.1 | 83.3 |
|-----------------------------------------|------|------|------|
| Hydrocarbon product distribution, wt.-%:|      |      |      |
| $C_7$-                                  | 0.26 | 0.46 | 0.44 |
| Di-isobutene                            | 90.0 | 84.4 | 82.5 |
| Other $C_8$                             | 0.49 | 0.82 | 1.03 |
| $C_9$ and heavier (~80% tri-isobutene)  | 9.25 | 14.3 | 16.0 |

The product also contained about 0.5 wt.-% ethers.

Preferred dimerization conditions when utilizing a resin catalyst comprise a liquid hourly space velocity (LHSV) with respect to isobutene of 0.1 to 3.0, with LHSV of 0.5 to 2.0 being preferred, based on fresh feed (i.e., excluding recycle). Reaction temperature generally ranges between 55° and 160° C., with a preferred temperature range of about 100° to 130° C. There may be a temperature gradient through the bed, which preferably is no greater than about 10° to 25° C. The reaction is carried out under sufficient pressure to maintain a liquid phase system, e.g., 1.5 to 2.5 MPa.

A well known alternative catalyst for the dimerization process is a solid phosphoric acid (SPA) catalyst. The SPA catalyst refers to a solid catalyst that contains as a principal ingredient an acid of phosphorus such as ortho-, pyro- or tetraphosphoric acid. The catalyst is normally formed by mixing the acid of phosphorus with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15-30% of the catalyst, with the remainder being the phosphoric acid. The additive may comprise about 3-20% of the total carrier material. Variations from this such as a lower phosphoric acid content are however possible. Further details as to the composition and production of SPA catalysts may be obtained from U.S. Pat. Nos. 3,050,472; 3,050,473; and 3,132,109 and from other references.

When utilizing the alternative SPA catalyst, dimerization conditions comprise a preferred temperature in the reaction zone of from about 90° to 260° C., and more typically in a range of from about 150° to 230° C. Pressures within the dimerization reaction zone will usually be in a range of from 200 kPa to 8 MPa, and more typically in a range of from 1.4 to 4 MPa. Steam or water may be fed into the reactor to maintain the desired water content in the preferred catalyst.

Effluent from the dimerization zone is stabilized to separate overhead unconverted isobutene along with butanes and lighter hydrocarbons. The stabilizer overhead may be recycled to the dimerization zone for further conversion of the isobutene as well as for temperature control of the reaction. The stabilized butene dimer, comprising one or both of iso-octenes and iso-octanes, comprises the feed to the aromatization zone.

The unconverted butenes and butanes recovered from the overhead of the dimerization-zone stabilizer, along with a similar stream separated from the products of the aromatization zone, preferably are treated to obtain a butane recycle stream to one or both of the dehydrogenation zone and the deisobutanizer in order to recover isobutane for further processing. After stabilization to remove $C_3$ and lighter materials, the butene-butane stream is charged to a hydrogenation zone. This zone is designed to fully saturate all the hydrocarbons charged thereto while minimizing any cracking or polymerization. As a result, the hydrogenation may take on any form known in the art, but preferably comprises a fixed-bed reaction zone in which all of the entering materials are contacted with a hydrogenation catalyst at hydrogenation conditions. A broad range of hydrogenation conditions includes an LHSV (liquid hourly space velocity based at 15° C. liquid) between about 0.5 and 20, a pressure between 150 kPa and 3.5 MPa, and a temperature of 50° to 500° C. A preferred range of hydrogenation conditions includes an LHSV of 4 to 20, a pressure of 0.8 to 2.2 MPa, and a temperature of 200° to 400° C. Hydrogen is passed through the hydrogenation zone either on a once-through basis or recycled by compression after separation.

A broad range of catalysts are commercially available for the hydrogenation zone. Suitable catalyst for this process will completely saturate mono- and polyolefinic hydrocarbons without significant cracking or polymerization activity. Such catalysts will normally comprise one or more metallic components as an elemental metal or a metal compound. The metals are normally chosen from Groups VII and IVA of the Periodic Table of the elements such as nickel, platinum, palladium and tin. Platinum is a preferred metal in these catalysts. Based on the weight of the metal, the catalyst may contain from 0.1 to 4.0 wt. % metallic components. The metallic components of the catalyst are supported by a refractory inorganic oxide material such as one of the aluminas, silica, silica-alumina mixtures, various clays and natural or synthetic zeolitic materials. Preferably, the carrier material comprises alumina. Metallic components may be added to the carrier which is in the form of spheres, pellets or extrudates by impregnation, cogelation or coprecipitation. Preferably, the metallic components are impregnated by immersing an extruded particle in an aqueous solution of a metal-containing compound and thereafter treating the impregnated particle by drying, calcination or other treatments.

The product of the hydrogenation zone is stabilized for removal of light components and preferably returned to the deisobutanizer for recovery of isobutane and normal butane for further processing as described hereinabove.

It is within the scope of the present invention that part or all of the butene dimer is processed in a dimer hydrogenation zone before being passed to the aromatization zone. Suitable conditions and catalysts for dimer hydrogenation are taught in U.S. Pat. Nos. 5,847,252; 5,856,604 and 6,025,533, incorporated herein by reference thereto. The hydrogenation zone would yield a hydrogenated dimer comprising 2,2,4-trimethylpentane and 2,5-dimethylhexane along with unconverted butene dimer as feed to the aromatization zone. This optional hydrogenation would also generate part if not all of the heat required to convert partially or fully hydrogenated butene dimer to aromatics. Preferably, however, the stabilized butene dimer is not fully hydrogenated before passing to the aromatization zone.

The butene dimer passing to the aromatization zone comprises a high concentration of one or more of 2,4,4-trimethylpentene, 2,2,4-trimethylpentane, 2,5-dimethylhexene and 2,5-dimethylhexane. The present process is particularly effective for the aromatization of butene dimer that is not fully hydrogenated, namely a feed stream containing some 2,4,4-trimethylpentene, which is less readily converted in processes of the known art.

The aromatization process may be effected in a reactor section comprising one reactor or in multiple reactors with provisions known in the art to adjust inlet temperatures to individual reactors. The feed may contact the catalyst system in each of the respective reactors in either upflow, downflow, or radial-flow mode. Since the preferred aromatization process operates at relatively low pressure, the low pressure drop in a radial-flow reactor favors the radial-flow mode. As the predominant dehydrocyclization reaction is endothermic, the reactor section generally will comprise two or more reactors with interheating between reactors to compensate for the endothermic heat of reaction and maintain dehydrocyclization conditions.

The reactor section usually is associated with catalyst-regeneration options known to those of ordinary skill in the art, such as: (1) a semiregenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst become deactivated and the catalyst in the isolated reactor is regenerated and reactivated while the other reactors remain on-stream; (3) a moving-bed reactor with continuous catalyst withdrawal, regeneration, reactivation and substitution of the reactivated catalyst, permitting higher operating severity by maintaining high catalyst activity through regeneration cycles of a few days; (4) a hybrid system with semiregenerative and continuous-regeneration provisions in the same unit; (5) an ebullated-bed reactor with continuous catalyst withdrawal and regeneration; (6) a continuously stirred tank reactor; or (7) a riser-reactor reforming process, generally associated with a fluidized reactor and continuous catalyst regeneration according to U.S. Pat. No. 5,565,090 which is incorporated herein by reference. The preferred embodiment of the present invention is a moving-bed reactor with continuous catalyst regeneration.

An aromatization catalyst preferably incorporates porous, adsorptive, high-surface-area materials. Within the scope of the present invention are refractory supports containing one or more of: (1) refractory inorganic oxides such as alumina, silica, titania, magnesia, zirconia, chromia, thoria, boria or mixtures thereof; (2) synthetically prepared or naturally occurring clays and silicates, which may be acid-treated; (3) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations; (4) spinels such as $MgAl_2O_4$, $FeAl_2O_4$, $ZnAl_2O_4$; and (5) combinations of materials from one or more of these groups.

The preferred support optimally comprises a porous, adsorptive, high-surface-area inorganic oxide having a surface area of about 25 to about 500 $m^2/g$. The porous support preferably is uniform in composition and relatively refractory to the conditions utilized in the process. By the term "uniform in composition," it is meant that the support be unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention refractory inorganic oxides such as alumina, titania, zirconia, chromia, zinc oxide, magnesia, thoria, boria, silica-alumina, silica-magnesia, chromia-alumina, alumina-boria, silica-zirconia and other mixtures thereof. The preferred support is substantially free of microcrystalline porous material, i.e., molecular sieves, and in particular contains less than about 1.0 wt.-% of zeolitic materials.

Favored refractory inorganic oxides for use in the present invention comprise one or more of alumina, magnesia, titania, and zirconia, with alumina being particularly favored. Suitable alumina materials are the crystalline aluminas known as the theta-, alpha-, gamma-, and eta-alumina, with theta-, alpha-, and gamma-alumina giving favorable results and theta-alumina being particularly preferred. An especially favored catalyst comprises at least about 80 wt.-% theta alumina. Magnesia, alone or in combination with alumina, comprises an alternative inorganic-oxide component of the catalyst and provides the required nonacidity. The preferred refractory inorganic oxide will have an apparent bulk density of about 0.3 to about 1.1 g/cc and surface area characteristics such that the average pore diameter is about 20 to 1000 angstroms, the pore volume is about 0.05 to about 1 cc/g, and the surface area is about 50 to about 500 $m^2/g$.

It is essential that the catalyst be non-acidic, as acidity lowers the selectivity to para-xylene of the finished catalyst. The required nonacidity may be effected by any suitable method, including impregnation, co-impregnation with a platinum-group metal, or ion exchange. Impregnation of one or more of the alkali and alkaline earth metals, especially potassium, in a salt solution is favored as being an economically attractive method to neutralize the acidity of the support as well as to modify the hydrogenation metal. The alkali or alkaline earth metal effectively is associated with an anion such as hydroxide, nitrate or a halide such as chloride or bromide consistent with nonacidity of the finished catalyst, with a nitrate being favored. Optimally, the support is cold-rolled with an excess of solution in a rotary evaporator in an amount sufficient to provide a nonacidic catalyst. The alkali or alkaline earth metal may be coimpregnated along with a platinum-group metal component, as long as the platinum-group metal does not precipitate in the presence of the salt of the alkali or alkaline earth metal.

Ion exchange is an alternative method of incorporating nonacidity into the catalyst. The inorganic-oxide support is contacted with a solution containing an excess of metal ions over the amount needed to effect nonacidity. Although any suitable method of contacting may be used, an effective method is to circulate a salt solution over the support in a fixed-bed loading tank. A water-soluble metal salt of an alkali or alkaline earth metal is used to provide the required metal ions; a potassium salt is particularly preferred. The support is contacted with the solution suitably at a temperature ranging from about 10° to about 100° C.

The nonacidity of the aromatization-catalyst support may be determined using a variety of methods known in the art. A preferred method of determining acidity is the heptene-cracking test: conversion of heptene, principally by cracking, isomerization and ring formation, is measured at specified conditions, with cracking being particularly indicative of the presence of strong acid sites. Alternatively, nonacidity may be characterized by the ACAC (acetonylacetone) test, in which ACAC is converted over the support to be tested at specified conditions: dimethylfuran in the product is an indicator of acidity, while methylcyclopentenone indicates basicity. Another useful method of measuring acidity is $NH_3$-TPD (temperature-programmed desorption) as disclosed in U.S. Pat. No. 4,894,142, incorporated herein by reference; the $NH_3$-TPD acidity strength should be less than about 1.0. Other methods such as $_{31}P$ solids NMR of adsorbed TMP (trimethylphosphine) also may be used to measure acidity. Suitable methods of characterizing nonacidity are described in more detail in U.S. Pat. No. 5,831,139.

An alternative suitable support having inherent nonacidity may be termed a "synthetic hydrotalcite" characterized as a layered double hydroxide or metal-oxide solid solution. Hydrotalcite is a clay with the ideal unit cell formula of $Mg_6Al_2(OH)_{16}(CO_3).4H_2O$, and closely related analogs with variable magnesium/aluminum ratios may be readily prepared. These embodiments are solid solutions of a divalent metal oxide and a trivalent metal oxide having the general formula $(M^{+2}_xO)(M^{+3}_yO)OH_y$, derived by calcination of synthetic hydrotalcite-like materials whose general formula may be expressed as $(M^{+2})_x(M^{+3})_y(OH)_zA_q.rH2O$. $M^{+2}$ is divalent metal or combination of divalent metals selected from the group consisting of magnesium, calcium, barium, nickel, cobalt, iron, copper and zinc. $M^{+3}$ is a trivalent metal or combination of trivalent metals selected from the group consisting of aluminum, gallium, chromium, iron, and lanthanum. Both $M^{+2}$ and $M^{+3}$ may be mixtures of metals belonging to the respective class: for example, $M^{+2}$ may be pure nickel or may be both nickel and magnesium, or even nickel-magnesium-cobalt; $M^{+3}$ may be solely aluminum or a mixture of aluminum and chromium, or even a mixture of three trivalent metals such as aluminum, chromium, and gallium. $A_q$ is an anion, most usually carbonate although other anions may be employed equivalently, especially anions such as nitrate, sulfate, chloride, bromide, hydroxides, and chromate. The ratio x/y of the divalent and trivalent metals can vary between about 2 and about 20, with the ratios of 2 to about 10 being preferred. The case where $M^{+2}$ is magnesium, $M^{+3}$ is aluminum, and A is carbonate corresponds to the hydrotalcite series. Calcination of such layered double hydroxides results in destruction of the layered structure and formation of materials which are effectively described as solid solutions of the resulting metal oxides. It is preferable that the $(M^{+2}{}_xO)(M^{+3}{}_yO)OH_y$ solid solution has a surface area at least about 150 m²/g, more preferably at least 200 m²/g and it is even more preferable that it be in the range from 300 to 350 m²/g. Preparation of Suitable Basic Metal-Oxide Supports is Described in Detail in U.S. Pat. No. 5,254,743.

An inorganic-oxide powder may be formed into a suitable catalyst material according to any of the techniques known to those skilled in the catalyst-carrier-forming art. Spherical carrier particles may be formed, for example, from the preferred alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to an alumina support by known methods; (2) forming an extrudate from the powder by established methods and thereafter rolling the extrudate particles on a spinning disk until spherical particles are formed which can then be dried and calcined to form the desired particles of spherical support; and (3) wetting the powder with a suitable peptizing agent and thereafter rolling the particles of the powder into spherical masses of the desired size. The powder can also be formed in any other desired shape or type of support known to those skilled in the art such as rods, pills, pellets, tablets, granules, extrudates, and like forms by methods well known to the practitioners of the catalyst material forming art.

The favored form of the preferred non-zeolytic catalyst support is a sphere. Alumina-bound spheres may be continuously manufactured by the well known oil-drop method which comprises: forming an alumina hydrosol by any of the techniques taught in the art and preferably by reacting aluminum metal with hydrochloric acid; combining the resulting hydrosol with the zeolite and a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and an ammoniacal solution to further improve their physical characteristics. The resulting aged and gelled particles are then washed and dried at a relatively low temperature of about 150° to about 205° C. and subjected to a calcination procedure at a temperature of about 450° to about 700° C. for a period of about 1 to about 20 hours. This treatment effects conversion of the alumina hydrogel to the corresponding crystalline gamma-alumina. U.S. Pat. No. 2,620,314 provides basic details and is incorporated herein by reference thereto.

In an alternative embodiment, the aromatization catalyst comprises a non-acidic large-pore molecular sieve. Suitable molecular sieves generally have a maximum free channel diameter or "pore size" of 6 Å or larger, and preferably have a moderately large pore size of about 7 to 8 Å, and materials containing a significant amount of external surface. Such molecular sieves include those characterized as LTL, BPH, OFF, MOR, MTW, FAU, AFI, BEA or MWW structure type by the IUPAC Commission on Zeolite Nomenclature, with the LTL structure being preferred. It is essential that the preferred L-zeolite be non-acidic, as acidity in the zeolite lowers the selectivity to aromatics of the finished catalyst. In order to be "non-acidic," the zeolite has substantially all of its cationic exchange sites occupied by nonhydrogen species. Preferably the cations occupying the exchangeable cation sites will comprise one or more of the alkali and alkaline earth metals, particularly Li, Na, K, Rb, Cs, Mg, Ca, Sr and Ba. Other cationic species may be present alternatively or in addition to the foregoing. An especially preferred nonacidic L-zeolite is potassium-form L-zeolite.

A favored molecular sieve utilized in the alternative aromatization catalyst has a unit empirical formula on an anhydrous basis of:

where "A" is at least one exchangeable cation selected from the group consisting of alkali and alkaline earth metals, "S" is a metal comprising one or more of Sn, Zn, B, In, Ga and Ge, "m" is the mole fraction of A and varies from about 0.01 to about 0.49, "w" is the mole fraction of metal and varies from about 0.01 to about 0.49, "x" is the mole fraction of aluminum and varies from about 0.01 to about 0.49 and "y" is the mole fraction of silicon and varies from about 0.50 to about 0.98. An especially preferred molecular sieve utilizes tin as the metal in the above formula, which then becomes:

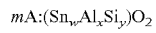

Such favored molecular sieves are conveniently prepared by the technique disclosed in U.S. Pat. No. 5,518,708 which teachings are incorporated by reference. Generally, the process involves contacting a crystalline zeolite having a molar $SiO_2/Al_2O_3$ ratio of at least 2 with an effective amount of a fluoro salt of tin, preferably in an amount of at least 0.0075 moles per 100 grams of zeolite starting material, the fluoro salt preferably being in the form of an aqueous solution or slurry which is contacted with the zeolite either incrementally or continuously at a slow rate (optionally in the presence of a buffer) whereby framework aluminum atoms of the zeolite are removed and replaced by tin atoms while retaining at least 80 percent and more preferably at least 90 percent of the crystal structure of the starting zeolite.

The fluoro salt preferably is provided as an aqueous solution or slurry, but solutions or slurries employing alcohols or other organic solvents may be suitable alternatives. An effective amount of fluoro salt is that amount which provides sufficient fluoride and tin for the process and the desired amount of tin in the final molecular sieve product. Solutions having fluoro salt concentrations of between about $10^{-3}$ moles per liter of solution and up to saturation of the solution can be employed, but preferably concentrations of between about 0.5 and about 1.0 moles per liter of solution are used. The minimum value for the amount of fluoro salt to be added is usually at least equivalent to the minimum mole fraction of aluminum to be removed from the zeolite.

The solution or slurry is maintained at an effective pH such that, under effective process conditions, a monomeric species of the tin is present in the reaction solution and the pH is high enough to avoid undue destructive acidic attack on the particular zeolite. The effective pH value generally is greater than 1, preferably greater than 3 and more preferably in the range of about 3 to about 7. Crystal degradation of many zeolites is found to be unduly severe at pH values below about 3, whereas insertion of the tin may be slow from a practical standpoint as a result of the solubility of tin at a pH of 7 and above.

The fluoro salt used as the aluminum extractant and as the source of tin can be any of the fluoro salts having the general formula:

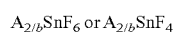

where "A" is a metallic or non-metallic cation having a valence "b" including alkylammonium, $H^+$, $NH_4^+$, $Mg^{++}$, $Li^+$, Na$^+$, K$^+$, Ba$^{++}$, Cd$^{++}$, Cu$^{++}$, Ca$^{++}$, Cs$^+$, Fe$^{++}$, Co$^{++}$, Pb$^{++}$, Mn$^{++}$, Rb$^+$, Ag$^+$, Sr$^{++}$, Tl$^+$ and Zn$^{++}$. The ammonium and hydronium cation forms of the fluoro salt are generally preferred because of their solubility in water and also because these cations form water soluble by-product salts upon reaction with the zeolite, e.g., (NH$_4$)$_3$AlF$_6$ and/or (NH$_4$)$_2$AlF$_5$. Other salts which may be used include a combination of salts of SnF$_2$ and $^3$/$_2$(NH$_4$HF$_2$) or SnF$_4$ and NH$_4$ HF$_2$. Preferred fluoro salts are NH$_4$SnF$_3$; SnF$_2$.$^3$/$_2$(NH$_4$HF$_2$) and SnF$_4$.NH$_4$HF$_2$.

The preferred effective reaction temperature is between about 10° C. and about 99° C., preferably between about 20° and 95° C., but temperatures of 125° C. or higher and as low as 0° C. may be employed in some cases. Reaction temperature and reagent concentrations are optimized with respect to the zeolite starting material to provide adequate time for insertion of framework tin consistent with practical commercial considerations. Generally more highly siliceous zeolites enable higher permissible reaction temperatures and lower pH conditions.

In specifying the proportions of the zeolite starting materials or adsorption properties of the zeolite product and the like herein, the "anhydrous state" of the zeolite will be intended unless otherwise stated. The term "anhydrous state" is employed herein to refer to a material substantially devoid of both physically adsorbed and chemically adsorbed such as is typically obtained by heating the zeolite in dry air at about 450° C. for about 4 hours.

It is preferable to composite zeolite with a binder in order to provide a convenient form for use in the catalyst particles of the present invention. The art teaches the suitability of a variety of refractory inorganic oxide binders. One or more of silica, alumina or magnesia are preferred binder materials of the present invention. One or both of amorphous silica and alumina are especially preferred. In one embodiment, excellent results are obtained when using a synthetic white silica powder precipitated as ultra-fine spherical particles from a water solution. A silica binder preferably is nonacidic, contains less than 0.3 wt.-% sulfate salts, and has a BET surface area of from about 120 to 160 m$^2$/g.

The zeolite and binder may be composited to form particle shapes known to those skilled in the art such as spheres, extrudates, rods, pills, pellets, tablets or granules. The preferred form of a zeolite-containing aromatization catalyst is a cylindrical extrudate. In one method of forming extrudates, potassium-form L-zeolite and amorphous silica are commingled as a uniform powder blend prior to introduction of a peptizing agent. An aqueous solution comprising sodium hydroxide or potassium hydroxide is added to form an extrudable dough. The dough preferably will have a moisture content of from 30 to 50 wt.-% in order to form extrudates having acceptable integrity to withstand direct calcination. The resulting dough is extruded through a suitably shaped and sized die to form extrudate particles, which are dried and calcined generally by known methods. Preferably, extrudates are subjected directly to calcination without an intermediate drying step in order to encapsulate potassium ions and preserve basicity. The calcination of the extrudates is is effected in an oxygen-containing atmosphere at a temperature of from about 260° to 650° C. for a period of about 0.5 to 2 hours.

An essential ingredient of the aromatization catalyst is a metal component comprising at least one metal selected from Groups VIII (IUPAC 8-10) and IA of the Periodic Table, including the platinum-group metals, Fe, Co, Ni, Cu, Ag and Au. Of the preferred Group VIII platinum-group metals, i.e., platinum, palladium, rhodium, ruthenium, osmium and iridium, platinum is particularly preferred. Mixtures of platinum-group metals as a uniformly distributed component or platinum-group surface metals also are within the scope of this invention. The platinum-group metal component may exist within the final catalytic composite as a compound such as an oxide, sulfide, halide, or oxyhalide, in chemical combination with one or more of the other ingredients of the composite, or as an elemental metal. Best results are obtained when substantially all of the metals are present in the elemental state. The platinum-group metal component may be present in the final catalyst composite in any amount which is catalytically effective, but relatively small amounts are preferred. The uniformly distributed platinum-group metals generally will comprise from about 0.01 to 5 wt.-% of the final catalyst, and preferably about 0.05 to 2 wt.-%, calculated on an elemental basis.

The preferred platinum-group metal component may be incorporated into the aromatization catalyst in any suitable manner such as coprecipitation or cogellation with the carrier material, ion exchange or impregnation. Impregnation using water-soluble compounds of the metal is preferred. Typical platinum-group compounds which may be employed are chloroplatinic acid, ammonium chloroplatinate, bromoplatinic acid, platinum dichloride, platinum tetrachloride hydrate, tetraamine platinum chloride, tetraamine platinum nitrate, dinitrodiaminoplatinum, platinum dichlorocarbonyl dichloride, palladium chloride, palladium chloride dihydrate, palladium nitrate, and the like. Chloroplatinic acid or tetraamine platinum chloride are preferred as the source of the preferred platinum component.

The aromatization catalyst may contain a halogen component. The halogen component may be either fluorine, chlorine, bromine or iodine or mixtures thereof with chlorine being preferred. Considering the nonacidic nature of the support, the halogen usually is incorporated into the catalyst only in association with the incorporation of a metal component. The halogen component is generally present in a combined state with the inorganic-oxide support. The halogen component is preferably well distributed throughout the catalyst and may comprise from more than 0.2 to about 15 wt.-% calculated on an elemental basis, of the final catalyst.

It is within the scope of the present invention that the aromatization catalyst may contain supplemental metal components known to modify the effect of the preferred platinum component. Such metal modifiers may include one or more of the Group IVB (IUPAC 14) metals, Group 1b (IUPAC 11) metals, rhenium, indium, gallium, bismuth, zinc, uranium, thallium and the rare earth (lanthanide) metals. Group VIa (IUPAC 6) metals are disfavored, considering the known toxicity of chromium. One or more of tin, indium, germanium, gallium, copper, silver, gold, lead, zinc and the rare-earth elements are favored modifier metals, with tin, indium, germanium, cerium and lead being particularly favored. If present, the concentration of a metal modifier in the catalyst may be within the range of 0.001 to 5.0 wt.-%. Catalytically effective amounts of such metal modifiers may be incorporated into the catalyst by any means known in the art.

The final aromatization catalyst generally will be dried at a temperature of from about 100° to 320° C. for about 0.5 to 24 hours, followed by oxidation at a temperature of about 300° to 550° C. in an air atmosphere which preferably contains a chlorine component for 0.5 to 10 hours. Preferably the oxidized catalyst is subjected to a substantially water-free reduction step at a temperature of about 300° to 550° C. for 0.5 to 10 hours or more. The duration of the reduction step should be only as long as necessary to reduce the platinum, in order to avoid pre-deactivation of the catalyst, and may be performed in-situ as part of the plant startup if a dry atmosphere is maintained.

The butene dimer contacts the aromatization catalyst in the aromatization zone at aromatization conditions to obtain an aromatized effluent, with the principal reaction being dehydrocyclization of olefinic and paraffinic hydrocarbons to obtain xylenes having a higher-than-equilibrium concentration of para-xylene. Aromatization conditions include a pressure of from about 100 kPa to 6 MPa (absolute), with the preferred range being from 100 kPa to 1 MPa (absolute) and a pressure of about 300 kPa or less at the exit of the last reactor often yielding particularly favorable results. The volume of the contained aromatization catalyst corresponds to a liquid hourly space velocity of from about 0.5 to 40 $hr^{-1}$. Free hydrogen as molecular $H_2$ is supplied to the aromatization zone in an amount sufficient to correspond to a ratio of from about 0.1 to 10 moles of hydrogen per mole of hydrocarbon feedstock; other components of a hydrogen-containing gas stream may comprise one or more of hydrocarbons, nitrogen and steam. The operating temperature, defined as the maximum temperature of the combined hydrocarbon feedstock, free hydrogen, and any components accompanying the free hydrogen, generally is in the range of 260° to 600° C. Hydrocarbon types in the feed stock also influence temperature selection.

In an optional embodiment of the invention, the aromatization zone comprises a hydrogenation reactor to contact the butene dimer with a hydrogenation catalyst to convert olefins to paraffins prior to the aromatization step. The hydrogenation reactor utilizes operating conditions as described above, except that the operating temperature generally is lower and usually is within the range of 150° to 300° C. Suitable hydrogenation catalysts comprise one or more metallic components as an elemental metal or a metal compound. The metals are normally chosen from Groups VIII and IVA of the Periodic Table of the elements such as nickel, platinum, palladium and tin. Platinum is a preferred metal in these catalysts. Based on the weight of the metal, the catalyst may contain from 0.1 to 4.0 wt. % metallic components. The metallic components of the catalyst are supported by a refractory inorganic oxide material such as one of the aluminas, silica, silica-alumina mixtures, various clays and natural or synthetic zeolitic materials. Preferably, the carrier material comprises alumina.

The aromatization zone produces an aromatics-rich product, with the aromatics content of the $C_5$+ portion of the effluent typically within the range of about 45 to 95 wt.-%, and more usually more than about 85 wt.-%. The composition of the aromatics will depend principally on the feedstock composition and operating conditions. From the present dimerized isobutene feedstock, the aromatics consist principally of $C_8$ aromatics with a high para-xylene content.

Using techniques and equipment known in the art, the aromatics-rich effluent from the aromatization zone usually is passed through condensing and cooling facilities to a separator. A hydrogen-rich gas is separated and recycled through suitable compressing means to the first reactor of the aromatization zone, with some net hydrogen available for other uses. The liquid phase from the separation zone is normally withdrawn and processed in a fractionating system.

The aromatization-zone product is fractionated by conventional means to separate $C_4$ and lighter materials, which may be returned to the light-ends processing section of the dimerization zone in order to recycle butanes to the deisobutanizer. $C_5$ to $C_7$ hydrocarbons are removed by fractionation for blending into gasoline or processing in conventional refining units for recovery of benzene and toluene values. Mixed $C_8$ aromatics, representing a para-xylene concentrate, are recovered overhead in a rerun column, with the bottoms stream, comprising Cg and heavier aromatics, being a desirable component for blending into premium gasoline. Optionally, the para-xylene concentrate is separated from $C_5$ to $C_7$ hydrocarbons and Cg and heavier aromatics in a sidestream fractionator.

The xylene yield relative to conversion of butene dimer in the aromatization zone generally is at least about 15 wt.-%, and more usually 25 wt.-% or more. A xylene yield of about 35 to 40 wt.-% or more often is attainable in the present process.

In conjunction with the above xylene yields, the concentration of para-xylene in xylenes as represented by the para-xylene concentrate will be significantly above the equilibrium value of 20 to 25 wt.-%. Para-xylene concentration in the xylenes usually will be about 50 wt.-% or more, and often at least about 60 wt.-%. Concentrations of about 70 wt.-% or more of para-xylene in xylenes are achievable, and a concentration of about 85 wt.-% enables ready use of single-stage crystallization for para-xylene recovery.

At least a portion of the para-xylene concentrate is passed to the para-xylene purification zone. This zone comprises any suitable process for recovering high-purity para-xylene product. Suitable processes may include one or more of crystallization, simulated-moving-bed adsorption, pressure-swing adsorption and fractionation. An integrated adsorption and crystallization process is described in U.S. Pat. No. 5,329,060, the provisions of which are incorporated herein by reference. Crystallization, and especially single-stage crystallization, is preferred for para-xylene separation from the para-xylene concentrate of the present invention.

Para-xylene recovery by crystallization from mixed $C_8$ aromatics is well known. U.S. Pat. Nos. 2,866,833 and 2,985,694 describe multi-stage crystallization processes for para-xylene recovery. Such processes have the disadvantage of low para-xylene recovery due to the formation of eutectic binaries in the mother liquor from which the para-xylene crystals are recovered as well as high operating costs resulting from the multiple stages. U.S. Pat. No. 5,319,060 teaches overcoming this disadvantage by using selective adsorption to enrich the para-xylene feed to crystallization, enabling the use of single-stage crystallization. The relevant contents of the above patents are incorporated herein by reference thereto.

Feed generally enters a crystallizer near the top and exits near the bottom. Each crystallizer is usually equipped with scrapers that remove crystals adhering to the internal walls of the vessel. Crystallizer slurry can be recirculated to the crystallizer to classify the crystals within the crystallizer. Effluent from the crystallizer is passed to a centrifuge, which operates to separate the mother liquor from the para-xylene crystals.

Since the concentration of para-xylene in the mixed $C_8$ aromatics is relatively high, generally in excess of 70 wt.-% and more usually at least about 85 wt.-%, a purification zone comprising crystallization usually can be reduced to a single stage. This stage can be operated at purification conditions approximating those of the final stage of multi-stage crystallization, for example, temperatures of 0 to −10° C. Chilling usually can be provided by propane vaporization. The crystallization is limited only by the amount of solids that can readily flow in a stream rather than the previously mentioned eutectic limit. At least a portion of the mother liquor can be recycled and mixed with the crystallization feed to provide more liquor to carry additional recovered para-xylene, with the remaining net portion being a desirable component for blending into premium gasoline. Alternatively or in addition, additional para-xylene can be recovered from the mother liquor which may comprise an to above-equilibrium concentration of para-xylene.

Optional additional treatment of the stage para-xylene crystals may include washing the crystals with a variety of compounds including but not limited to para-xylene product, normal pentane, toluene, aqueous alcohols and aqueous salts to improve final product purity by removing adhering second stage mother liquor. After melting the crystals, it may be necessary to feed the resulting mixture to a fractionation column to separate the para-xylene product from the wash liquor.

The high-purity para-xylene recovered from the purification zone comprises at least about 99.5 wt.-% para-xylene, and preferably at least about 99.7 wt.-% para-xylene.

Other embodiments and variants encompassed by and within the spirit of the present invention as claimed will be apparent to the skilled routineer. Examples follow which illustrate certain specific embodiments, and these particularly should not be construed to limit the scope of the invention as set forth in the claims.

EXAMPLES

Example 1

A catalyst comprising 18.6 wt.-% Cr and 3.41 wt.-% K on a gamma-alumina support was prepared following the procedure described in DuPont's patent application US0015026 A1. This catalyst serves as a comparative example of the known art for converting 2,2,4-trimethylpentane or 2,4,4-trimethylpentene to para-xylene, and is designated Catalyst X.

Example 2

A gamma-alumina sphere comprising 0.3 wt.-% Sn was impregnated with chloroplatinic acid (CPA) and 2 wt.-% HCl to give 0.29 wt.-% Pt. The impregnated support then was dried, oxychlorinated in the presence of air and HCl, and finally reduced in the presence of $H_2$. This catalyst of the known art is designated Catalyst Y.

Example 3

A theta-alumina sphere of 1/16-inch diameter prepared as described hereinabove and comprising 0.2 wt.-% Sn was impregnated with KCl and chloroplatinic acid (CPA) to give 0.45 wt.-% Pt and 0.70 wt.-% K. The impregnated support then was air calcined, conditioned in the presence of HCl and $Cl_2$, and finally reduced in the presence of $H_2$. This catalyst is designated as Catalyst A.

Example 4

A theta-alumina sphere of 1/16-inch diameter and comprising 0.2 wt.-% Sn was impregnated with KCl and chloroplatinic acid (CPA) to give 0.45 wt.-% Pt and 1.50 wt.-% K, and finished following the procedure described in Example 3. This catalyst is designated as Catalyst B.

Example 5

A theta-alumina sphere of 1/16-inch diameter and comprising 0.2 wt.-% Sn was impregnated with $CsNO_3$ and tetraamineplatinum nitrate (TAPN) to give 0.45 wt.-% Pt and 2.38 wt.-% Cs, and finished following the procedure described in Example 3. This catalyst is designated as Catalyst C.

Example 6

A gamma-alumina sphere of 1/32-inch diameter and comprising 0.57 wt.-% Sn was impregnated with $KNO_3$ and tetraamineplatinum nitrate (TAPN) to give 0.72 wt.-% Pt and 1.30 wt.-% K, and finished following the procedure described in Example 3. This catalyst is designated as Catalyst D.

Example 7

A theta-alumina sphere of approximately 1/32-inch diameter and comprising 0.57 wt.-% Sn was impregnated with $KNO_3$ and tetraamineplatinum nitrate (TAPN) to give 1.26 wt.-% and 0.70 wt.-% K, and finished following the procedure described in Example 3. This catalyst is designated as Catalyst E.

Example 8

Catalysts X and Y of the known art ("art") and catalysts A, B, C, D and E of the present invention ("inv.") were palletized into 20×40 mesh size and tested in the micro-reactor unit at atmospheric pressure with results as shown in Table 1. The catalysts, in reactor loadings from 250 to 1000 mg, were pre-reduced in the presence of $H_2$ at 450° C. The reactor was cooled to 300° C. and $H_2$ flow was directed through a bath of 2,2,4-trimethylpentane ("TMP") or 2,4,4-trimethylpentene ("TMP=") as indicated. The catalyst performance then was recorded at 500 and 550° C. based on data from non-polar and polar GC columns. The results show the catalysts of the present invention were significantly more effective than the catalysts of the known art in providing a combination of high xylene yields and high para-xylene content of the xylene product. None of the catalysts of the known art achieved a combination of 20% or higher xylene yield relative to conversion and 65% or higher para-xylene in the xylene product, levels which were achieved by all of the catalysts of the invention.

TABLE 1

| Catalyst | | | Temp. | Conversion | Xylenes | B/T/EB | $C_1$-$C_7$ | $C_4$+=$C_4$ | Xylenes/ | P-xylene/ |
| --- | --- | --- | --- | --- | --- | --- | --- | --- | --- | --- |
| Desig. | mg | Feed* | ° C. | wt. % | wt. % | wt. %# | wt. % | wt. %& | Conversion | Xylenes |
| X (art) | 500 | TMP | 500 | 7.48 | 0.14 | 0.46 | 6.74 | 5.27 | 1.9% | 79.7% |
| X (art) | 500 | TMP | 550 | 25.63 | 2.64 | 3.96 | 20.99 | 15.44 | 10.3% | 90.4% |
| A (inv.) | 250 | TMP | 500 | 18.31 | 3.99 | 4.50 | 8.93 | 4.98 | 21.8% | 74.0% |
| A (inv.) | 250 | TMP | 550 | 31.12 | 8.88 | 10.40 | 15.27 | 10.76 | 28.5% | 65.9% |
| A (inv.) | 1000 | TMP | 500 | 34.18 | 8.29 | 9.13 | 17.92 | 11.72 | 24.3% | 74.0% |
| A (inv.) | 1000 | TMP | 550 | 48.94 | 18.24 | 20.41 | 22.84 | 17.57 | 37.3% | 68.8% |
| X (art) | 1000 | TMP = | 500 | 34.17 | 0.73 | 1.64 | 30.63 | 24.89 | 2.1% | 62.5% |
| X (art) | 1000 | TMP = | 550 | 62.02 | 7.38 | 9.82 | 50.92 | 40.56 | 11.9% | 84.0% |
| Y (art) | 1000 | TMP = | 500 | 99.80 | 29.42 | 39.83 | 49.06 | 39.08 | 29.5% | 23.6% |
| Y (art) | 1000 | TMP = | 550 | 99.94 | 28.87 | 43.14 | 32.98 | 17.99 | 28.9% | 22.1% |
| A (inv.) | 1000 | TMP = | 500 | 32.19 | 13.91 | 14.63 | 11.90 | 4.01 | 43.2% | 70.9% |

TABLE 1-continued

| Catalyst | | | Temp. | Conversion | Xylenes | B/T/EB | $C_1$-$C_7$ | $C_4$ += $C_4$ | Xylenes/ | P-xylene/ |
|---|---|---|---|---|---|---|---|---|---|---|
| Desig. | mg | Feed* | °C. | wt. % | wt. % | wt. %[#] | wt. %[^] | wt. %[&] | Conversion | Xylenes |
| A (inv.) | 1000 | TMP = | 550 | 42.26 | 17.41 | 18.63 | 18.06 | 13.27 | 41.2% | 73.4% |
| B (inv.) | 1000 | TMP = | 550 | 37.09 | 9.20 | 9.93 | 21.90 | 18.38 | 24.8% | 77.6% |
| C (inv.) | 1000 | TMP = | 500 | 27.19 | 9.69 | 10.35 | 11.68 | 3.51 | 35.6% | 68.1% |
| C (inv.) | 1000 | TMP = | 550 | 42.74 | 15.88 | 17.17 | 19.17 | 14.24 | 37.2% | 72.3% |
| D (inv.) | 1000 | TMP = | 500 | 37.22 | 13.42 | 14.33 | 15.63 | 4.95 | 36.1% | 67.7% |
| D (inv.) | 1000 | TMP = | 550 | 52.23 | 23.80 | 25.49 | 19.77 | 14.14 | 45.6% | 69.2% |
| E (inv.) | 1000 | TMP = | 500 | 43.19 | 21.58 | 22.72 | 15.45 | 6.72 | 50.0% | 68.6% |
| E (inv.) | 1000 | TMP = | 550 | 52.24 | 24.75 | 26.55 | 20.06 | 14.57 | 47.4% | 70.2% |

*TMP is 2,2,4-trimethylpentane, TMP = is 2,4,4-trimethylpentene
[#]BTX is benzene, toluene and ethylbenzene
[^]$C_1$ to $C_7$ paraffins and olefins
[&]butanes + butenes, included in $C_1$-$C_7$

Example 9

A support prepared according to the known art, comprising 80 wt.-% K-L and 20 wt.-% alumina, was finished with tetraamineplatinum chloride (TAPC) and KCl to give 1.0 wt.-% Pt and 15 wt.-% K. This catalyst is designated as Catalyst Z.

Example 10

Ammonium-exchanged zeolite L was slurried in distilled water and heated to 75° C. A solution containing $SnF_4$ and $NH_4HF_2$ in distilled water was added incrementally over a period of 10 minutes to the zeolite. Following the addition of the tin solution, the slurry was digested over a period of 1.5 hours and the product was filtered and washed free of soluble fluoride. The solid product (NH4—Sn-L) was white and showed the characteristic crystal structure of zeolite L as indicated by X-ray powder diffraction.

The $NH_4$—Sn-zeolite L solid was slurried in distilled water, and the slurry was stirred and heated. KCl then was added and the mixture was allowed to react for 1½ hours, filtered, and the filtrate was washed with deionized water and calcined. This sample had the following metals contents: 0.57% Sn, 9.38% Al, 30.2% Si, and 13.7% K.

The calcined K—Sn-L was platinum impregnated using tetraamineplatinum chloride (TAPC) by evaporative impregnation to give a catalyst containing 0.39 wt.-% Pt and 0.57 wt.-% Sn. This catalyst is designated as Catalyst F.

Example 11

A similar catalyst was prepared following the procedure described in Example 10 to give 0.30 wt.-% Pt and 0.33 wt.-% Sn. This catalyst is designated as Catalyst G.

Example 12

The catalyst is prepared following the procedure described in Example 10 to give 0.60 wt.-% Pt and 0.33 wt.-% Sn. This catalyst is designated as Catalyst H.

Example 13

Catalysts were pelletized into 20×40 mesh size and evaluated in a micro-reactor unit at atmospheric pressure. The catalysts were pre-reduced in $H_2$ flow at 450° C. for 2 hours. The reactor then was cooled to 300° C. and hydrogen flow was directed through a 2,4,4-trimethylpentene bath and into the reactor. The catalyst performance is then collected at 500 and 550° C. based on data from non-polar and polar GC columns. The results as indicated in Table 2 show that catalysts F, G and H of the invention provide a combination of high xylene yields and high para-xylene content of the xylene product. Catalyst Z of the known art did not achieve a combination of 25% or higher xylene yield relative to conversion and about 50% or higher para-xylene in the xylene product, levels which were achieved by all of the catalysts of the invention.

TABLE 2

| Catalyst | | Temp. | Conversion | Xylenes | B/T/EB | $C_1$-$C_7$ | $C_4$ += $C_4$ | Xylenes/ | P-xylene/ |
|---|---|---|---|---|---|---|---|---|---|
| Desig. | mg | °C. | wt. % | wt. % | wt. %[#] | wt. %* | wt. %[&] | Conversion | Xylenes |
| Z (art) | 1000 | 500 | 62.04 | 25.12 | 38.54 | 22.52 | 8.71 | 40.5% | 36.1% |
| Z (art) | 1000 | 550 | 99.86 | 28.98 | 76.94 | 22.31 | 9.91 | 29.0% | 33.8% |
| A (inv.) | 1000 | 500 | 68.21 | 21.31 | 25.48 | 35.75 | 23.74 | 31.2% | 51.0% |
| A (inv.) | 1000 | 550 | 87.07 | 40.34 | 46.17 | 37.31 | 29.38 | 46.3% | 56.0% |
| B (inv.) | 1000 | 500 | 32.44 | 8.99 | 9.67 | 15.21 | 9.24 | 27.7% | 60.4% |
| B (inv.) | 1000 | 550 | 65.34 | 31.22 | 33.58 | 24.33 | 17.17 | 47.8% | 60.4% |
| C (inv.) | 1000 | 500 | 64.40 | 26.54 | 29.08 | 23.97 | 12.51 | 41.2% | 49.0% |
| C (inv.) | 1000 | 500 | 82.27 | 44.17 | 50.42 | 25.65 | 16.00 | 53.7% | 51.9% |

[#]BTX is benzene, toluene and ethylbenzene
*$C_1$ to $C_7$ paraffins and olefins
[&]butanes + butenes, included in $C_1$-$C_7$

Example 14

A catalyst of the art as found in the literature was prepared for comparison with selected catalysts in pilot-plant tests. Theta-alumina containing 0.3 wt % tin was impregnated to give 3.5 wt % Cr and 1.3 wt % of K. The catalyst is designated as Catalyst W.

Example 15

Catalysts A and H of the invention as previously described were tested further in a laboratory pilot plant under different sets of process conditions. In this test 10 ml of catalyst was loaded into a stainless-steel reactor. The catalyst was pre-reduced in $H_2$ flow at 450° C. for 2 hours. The reactor then was cooled to 300° C. and 2,2,4-trimethylpentane was introduced. Typical operating conditions comprised a plant pressure of 155 to 315 kPa, $H_2$ to hydrocarbon molar ratio of 1 to 4 and temperatures of about 500° to 560° C. as indicated. Products were analyzed by polar and non-polar GC columns to obtain the component breakdown. Results as shown in Table 3 demonstrated that both Pt—Sn—K supported on alumina (Catalyst A) and Pt—Sn—K-L (Catalyst H) are active and selective in converting 2,2,4-trimethylpentane to xylene with minimal formation of byproducts in comparison with the catalyst of the known art, and that the resulting xylenes have a para-xylene concentration significantly higher than that calculated based on thermodynamics.

TABLE 3

| Catalyst Desig. | Press. kPa | Temp. ° C. | Conversion wt. % | Xylenes wt. % | B/T/EB wt. %# | $C_1$-$C_7$ wt. %* | $C_4$+=$C_4$ wt. %& | Xylenes/ Conversion | P-xylene/ Xylenes |
|---|---|---|---|---|---|---|---|---|---|
| W (art) | 155 | 552 | 36.7 | 4.9 | 5.1 | 30.6 | 28.6 | 13.4% | 87.8% |
| A (inv.) | 315 | 559 | 88.6 | 31.2 | 34.8 | 39.0 | 31.5 | 35.2% | 60.8% |
| A (inv.) | 315 | 541 | 71.8 | 20.8 | 22.3 | 29.9 | 23.6 | 29.0% | 80.1% |
| A (inv.) | 200 | 512 | 43.9 | 21.0 | 28.6 | 6.3 | 5.2 | 47.8% | 75.2% |
| H (inv.) | 315 | 512 | 82.7 | 27.8 | 30.5 | 44.9 | 38.7 | 33.6% | 44.7% |
| H (inv.) | 190 | 503 | 72.3 | 52.1 | 53.2 | 8.0 | 6.6 | 72.1% | 46.6% |

BTX is benzene, toluene and ethylbenzene
*$C_1$ to $C_7$ paraffins and olefins
&butanes + butenes, included in $C_1$-$C_7$

We claim:

1. A process combination for the production of high-purity para-xylene from an isobutane concentrate comprising the steps of:
   a) contacting the isobutane concentrate with a dehydrogenation catalyst in a dehydrogenation zone operating at dehydrogenation conditions to produce hydrogen and a dehydrogenation product stream comprising isobutene;
   b) contacting at least a portion of the dehydrogenation product stream with a dimerization catalyst in a dimerization zone operating at dimerization conditions to produce a butene dimer comprising one or both of $C_8$ isoolefins and $C_8$ isoparaffins;
   c) contacting at least a portion of the butene dimer with a non-zeolitic aromatization catalyst in an aromatization zone operating at aromatization conditions to produce an para-xylene concentrate comprising xylenes having a higher-than-equilibrium content of para-xylene; and,
   d) passing at least a portion of the para-xylene concentrate to a para-xylene purification zone operating at purification-zone conditions to recover high-purity para-xylene;
   wherein the aromatization catalyst comprises:
   1) a support comprising an oxide of a metal selected from one or more of alumina, titania and zirconia;
   2) a hydrogenation metal selected from one or more of the platinum-group metals;
   3) a metal modifier selected from one or more of tin, indium, germanium, gallium, copper, silver, gold, lead, zinc and the rare-earth elements; and,
   4) one or more of the alkali and alkaline earth metals.

2. The process combination of claim 1 wherein the aromatization catalyst comprises the substantial absence of a Group VIB (6) metal.

3. The process combination of claim 1 wherein the support comprises at least about 80 wt.-% theta alumina.

4. A process combination for the production of high-purity para-xylene from a mixed butane feed comprising:
   a) processing the mixed butane feed in a deisobutanizer to separate an isobutane concentrate from a normal-butane concentrate;
   b) contacting at least a portion of the isobutane concentrate with a dehydrogenation catalyst in a dehydrogenation zone operating at dehydrogenation conditions to produce hydrogen and a dehydrogenation product stream comprising isobutene;
   c) contacting at least a portion of the dehydrogenation product stream with a dimerization catalyst in a dimerization zone operating at dimerization conditions to produce a butene dimer comprising one or both of $C_8$ isoolefins and $C_8$ isoparaffins;
   d) contacting at least a portion of the butene dimer with a non-zeolitic and nonacidic aromatization catalyst in an aromatization zone operating at aromatization conditions to produce a para-xylene concentrate comprising xylenes having a higher-than-equilibrium content of para-xylene;
   e) passing at least a portion of the para-xylene concentrate to a para-xylene purification zone operating at purification-zone conditions to recover high-purity para-xylene;
   wherein the aromatization catalyst comprises:
   1) a support comprising an oxide of a metal selected from one or more of alumina, titania and zirconia;
   2) a hydrogenation metal selected from one or more of the platinum-group metals;
   3) a metal modifier selected from one or more of tin, indium, germanium, gallium, copper, silver, gold, lead, zinc and the rare-earth elements; and,
   4) one or more of the alkali and alkaline earth metals.

5. The process combination of claim 4 further comprising contacting the normal-butane concentrate from step (a) with an isomerization catalyst in an isomerization zone operating at isomerization conditions to produce an isomerized product containing an increased content of isobutane, and passing the isomerized product to the deisobutanizer for recovery of additional isobutane concentrate.

6. The process combination of claim 4 further comprising recovering unconverted butenes and butanes by stabilization of the dimerization-zone product and the aromatization-zone product and contacting the unconverted butenes and butanes with a hydrogenation catalyst in a hydrogenation zone at hydrogenation conditions to obtain a butane recycle stream to one or both of the dehydrogenation zone and the deisobutanizer in order to recover isobutane for further processing.

7. The process combination of claim 4 wherein the dimerization catalyst of step (c) comprises a cationic resin.

8. The process combination of claim 4 wherein the dimerization catalyst of step (c) comprises solid phosphoric acid.

9. The process combination of claim 4 wherein step (c) comprises contacting the dehydrogenation product stream and an isobutane-containing stream with the dimerization catalyst which comprises an alkylation catalyst in the dimerization zone which comprises alkylation to produce a butene dimer which comprises a high concentration of $C_8$ isoparaffins.

10. The process combination of claim 4 wherein the aromatization conditions comprise a pressure of from about 100 kPa to 6 MPa (absolute), a hydrogen to hydrocarbon ratio of from about 0.1 to 1.0, a liquid hourly space velocity of from about 0.5 to 40 $hr^{-1}$, and an operating temperature of from about 260° to 600° C.

11. The process combination of claim 4 wherein the aromatization catalyst of step (d) comprises a non-zeolitic and nonacidic catalyst.

12. The process combination of claim 4 wherein the aromatization catalyst comprises the substantial absence of a Group VIB (6) metal.

13. The process combination of claim 4 wherein the support comprises at least about 80 wt.-% theta alumina.

14. The process combination of claim 4 wherein the xylene yield relative to conversion of butene dimer is at least about 15 wt.-% and the concentrate of para-xylene in the para-xylene concentrate is at least about 50 wt.-%.

15. The process combination of claim 4 wherein the xylene yield relative to conversion of butene dimer is at least about 15 wt.-% and the concentrate of para-xylene in the para-xylene concentrate is at least about 60 wt.-%.

16. The process combination of claim 4 wherein the high-purity paraxylene comprises at least about 99.7 wt.-% para-xylene.

17. A process combination for the production of high-purity para-xylene from a mixed butane feed comprising:
 a) processing the mixed butane feed in a deisobutanizer to separate an isobutane concentrate from a normal-butane concentrate;
 b) contacting the normal-butane concentrate with an isomerization catalyst in an isomerization zone operating at isomerization conditions to produce an isomerized product containing an increased content of isobutane, and passing the isomerized product to the deisobutanizer for recovery of additional isobutane concentrate;
 c) contacting at least a portion of the isobutane concentrate with a dehydrogenation catalyst in a dehydrogenation zone operating at dehydrogenation conditions to produce hydrogen and a dehydrogenation product stream comprising isobutene;
 d) contacting at least a portion of the dehydrogenation product stream with a dimerization catalyst in a dimerization zone operating at dimerization conditions to produce a butene dimer comprising one or both of $C_8$ isoolefins and $C_8$ isoparaffins and recover a stream of unconverted butenes and butanes;
 e) contacting at least a portion of the butene dimer with an aromatization catalyst in an aromatization zone operating at aromatization conditions produce an para-xylene concentrate comprising xylenes having a higher-than-equilibrium content of para-xylene and recover a stream of unconverted butenes and butanes;
 f) contacting the unconverted butenes and butanes from steps (d) and (e) with a hydrogenation catalyst in a hydrogenation zone at hydrogenation conditions to obtain a butane recycle stream to one or both of the dehydrogenation zone and the deisobutanizer in order to recover isobutane for further processing; and,
 g) passing at least a portion of the para-xylene concentrate to a para-xylene purification zone operating at purification-zone conditions to recover high-purity para-xylene.

* * * * *